US011739097B2

(12) United States Patent
Pouyet et al.

(10) Patent No.: US 11,739,097 B2
(45) Date of Patent: Aug. 29, 2023

(54) PROCESS FOR PRODUCING CHROMENES BY CATALYSIS WITH COPPER SALTS INTENDED FOR THE PREPARATION OF THERMOSETTING RESINS

(71) Applicants: ARIANEGROUP SAS, Paris (FR); CENTRE NATIONAL DE LA RECHERCHE SCIENTIFIQUE, Paris (FR); UNIVERSITE DE REIMS CHAMPAGNE-ARDENNE, Reims (FR)

(72) Inventors: Robin Pouyet, Le Haillan (FR); Xavier Coqueret, Reims (FR); Brigitte Defoort, Le Haillan (FR); Bastien Rivieres, Le Segur (FR)

(73) Assignees: ARIANEGROUP SAS, Paris (FR); CENTRE NATIONAL DE LA RECHERCHE SCIENTIFIQUE, Paris (FR); UNIVERSITE DE REIMS CHAMPAGNE-ARDENNE, Reims (FR)

( * ) Notice: Subject to any disclaimer, the term of this patent is extended or adjusted under 35 U.S.C. 154(b) by 680 days.

(21) Appl. No.: 16/937,044

(22) Filed: Jul. 23, 2020

(65) Prior Publication Data
US 2021/0024535 A1    Jan. 28, 2021

(30) Foreign Application Priority Data
Jul. 23, 2019   (FR) ...................................... 1908323

(51) Int. Cl.
*C07D 493/04* (2006.01)
*B01J 27/122* (2006.01)
*C08G 61/12* (2006.01)

(52) U.S. Cl.
CPC .......... *C07D 493/04* (2013.01); *B01J 27/122* (2013.01); *C08G 61/122* (2013.01); *C08G 2261/11* (2013.01); *C08G 2261/3242* (2013.01)

(58) Field of Classification Search
None
See application file for complete search history.

(56) References Cited

U.S. PATENT DOCUMENTS

| 5,155,196 | A | 10/1992 | Kolb et al. | |
|---|---|---|---|---|
| 11,591,343 | B2 | 2/2023 | Pouyet et al. | |
| 2003/0065187 | A1* | 4/2003 | Buchwald | C07C 209/10 548/557 |
| 2012/0309927 | A1* | 12/2012 | Kim | C08L 71/12 528/214 |
| 2019/0040178 | A1 | 2/2019 | Rivieres et al. | |

FOREIGN PATENT DOCUMENTS

| EP | 0 350 747 A2 | 1/1990 |
|---|---|---|
| EP | 2 842 951 A1 | 3/2015 |
| WO | WO 01/10861 A2 | 2/2001 |
| WO | WO 2017/129661 A1 | 8/2017 |

OTHER PUBLICATIONS

Wang "Cu-catalyzed intramolecular hydroarylation of alkynes", RSC Adv., 2014, 4, 61706-61710 (Year: 2014).*
Search Report as issued in French Patent Application No. 1908323, dated May 12, 2020.
Christoudoulou, M. S., et al., "Divergent Palladium- and Platinum-Catalyzed Intramolecular Hydroamination/Hydroarylation of O-Propargyl-2-aminophenols," European Journal of Organic Chemistry, vol. 44, Jul. 2018, XP055693802, pp. 6176-6184, Retrieved from the Internet: URL:https://chemistry-europe.onlinelibrary.wiley.com/doi/full/10.1002/ejoc.201801103 [Retrieved on May 11, 2020].
Al-Sader et al., "On the Mechanism of Flash Vacuum Pyrolysis of Phenyl Propargyl Ether. Intramolecular Deuterium Kinetic Isotope Effect on Claisen Rearrangement," J. Org. Chem., vol. 43, No. 18, (1978), XP55701628, pp. 3626-3627.
Parker, K. A., et al., "Electrocyclic Ring Closure of the Enols of Vinyl Quinones. A 2H-Chromene Synthesis," Organic Letters, vol. 3, No. 24, (2001), XP55701593, pp. 3875-3878.
Menon, R. S., et al., "The AU(I)-catalyzed Intramolecular hydroarylation of Terminal Alkynes Under Mild Conditions: Application to the Synthesis of 2H-Chromenes, Coumarins, Benzofurans, and Dihydroquinolines," J. Org. Chem., vol. 74, (2009), XP55082760, pp. 8901-8903.
Arcadi, A., et al., "Gold versus silver 1-7 catalyzed intramolecular hydroarylation reactions of [(3-arylprop-2-ynyl)oxy]benzene derivatives," Organic & Biomolecular Chemistry, vol. 10, No. 48, Jan. 2012, XP55700971, pp. 9700-9708.
Fang, W., et al., "Gold(I) catalyzed intramolecular hydroarylation and the subsequent ring enlargement of methylenecyclopropanes to cyclobutenes," RSC Advances, vol. 6, No. 46, Jan. 2016, XP55701069, pp. 40474-40479.
Sanglar, C., "Prepolymeres a Terminaisons Propargylique Et Chromene. Synthese, Etudes Physicochimiques, Mecanisms Et Cinetique D_E Polymerisation a L'Etat Fondu." Doctoral Thesis from L'Universite de Pau et des Pays de L'Adour, Centre Universitaire de Recherche Scientifique, Mention: Physicochimie des Polymers, Nov. 13, 1995, 132 pages, (with translation of relevant portions).

(Continued)

*Primary Examiner* — Nicole M. Buie-Hatcher
(74) *Attorney, Agent, or Firm* — Pillsbury Winthrop Shaw Pittman LLP

(57) ABSTRACT

A process for producing chromenes intended for the preparation of thermosetting resins, includes converting an aromatic propargyl ether of general formula (I) into a chromene by homogeneous catalysis with copper salts in anisole at a temperature between 100 and 170° C. Moreover, a process for preparing a material made of thermoset resin, includes successively a) carrying out the above process; b) polymerizing the reaction product obtained in a) so as to obtain the material made of thermoset resin; c) recovering the material made of thermoset resin obtained in b).

16 Claims, No Drawings

(56) References Cited

OTHER PUBLICATIONS

Liu, F., et al., "Blended Resins Based on a New Propargyl-Functional Resin: Synthesis, Cure, and Thermal Properties," Journal of Applied Polymer Science, vol. 102, pp. 4207-4212, (2006).
Hashmi, et al., "Modern Gold Catalyzed Synthesis," Wiley-VCH Verlag & Co. KGaA, (2012), 408 pages.
Godschaix, J. P., et al., "Acetylene-Chromene Terminated Resins as High Temperature Thermosets," 22$^{nd}$ International SAMPE Technical Conference, Nov. 1990, pp. 163-174.
Reghunadhan, C. P., et al., "Bis propargyl ether resins: synthesis and structure-thermal property correlations," European Polymer Journal 35 (1999) 235-246.
Dirlikov, S. K., et al., "Propargyl-terminated Resins—A Hydrophobic Substitute for Epoxy Resins," High Performance Polymers, vol. 2, No. 1, (1990), pp. 67-77.
Prat, D., et al., "CHEM21 selection guide of classical- and less classical-solvents," Green Chem., (2016), 18, pp. 288-296.
Dirlikov, S. K., et al., "Propargyl Terminated Resins (PTR): Preparation and Thermostability," Polym. Mater., vol. 59, (1988), pp. 990-993.
Efe, C., e al., "Gold nanoparticles supported on TiO2 catalyse the cycloisomerisation/ oxidative dimerisation of aryl propargyl ethers," Chem. Commun., (2011), vol. 47, pp. 803-805.
Echavarren, A. M., et al., "Chapter 1: Gold-Catalyzed Cyclizations of Alkynes With Alkenes and Arenes," Organic Reactions, vol. 92, (2017), 288 pages.
Dorel, R., et al., "Gold(I)-Catalyzed Activation of Alkynes for the Construction of Molecular Complexity," Chemical Reviews, (2015), vol. 115, pp. 9028-9072.
Rehman, H., et al., "Tandem Intramolecular Wittig and Claisen Rearrangement Reactions in the Thermolysis of 2-Methyl-2-Phenoxy-Propionyl-Cyanomethylenetriphenylphosphoranes: Synthesis of Substituted 2H-I-Benzopyrans and Benzofurans," Tetrahedron, vol. 43, No. 22, pp. 5335-5340, (1987).
Rehman, H., et al., "Synthesis of Benzofurans Via Tandem Intramolecular Wittig and 3,3-Signmatropic Reaction of Phenoxyacetyl-Cyanomethylenetriphenylphosphoranes," Synthetic Communications: An International Journal of Rapid Communications of Synthetic Organic Chemistry, (2006), 12 pages.
Ullenius, C., et al., "Formation of 2-Indanone and Benzocyclobutene from the Pyrolysis of Phenyl Ether," Department of Chemistry, University of Oregon, (1972), pp. 5911-5913.
Lazar, K. L., et al., "Optically detected magnetic resonance of α-deuterated 2-indanone," Journal of Luminescence, vol. 118, (2006), pp. 21-32.
Trahanovsky, W. S., et al., "Organic Oxalates. II. Formation of Bibenzyls by Pyrolysis of Benzyl Oxalates," Journal of the American Chemical Society, 90(11), (1968), pp. 2839 2842.
Non-Final Office Action as issued in U.S. Appl. No. 16/936,966, dated Jun. 9, 2023.

* cited by examiner

PROCESS FOR PRODUCING CHROMENES BY CATALYSIS WITH COPPER SALTS INTENDED FOR THE PREPARATION OF THERMOSETTING RESINS

CROSS REFERENCES TO RELATED APPLICATIONS

This application claims priority to French Patent Application No. 1908323, filed Jul. 23, 2019, the entire content of which is incorporated herein by reference in its entirety.

The present invention relates to the field of thermosetting resins, and materials obtained from these resins. These resins aim to replace phenolic resins in all applications in which the latter are used, in particular "ablative" materials.

An ablative material is defined as a material which is capable of undergoing ablation, that is to say a loss of substance by chemical decomposition, change of state or mechanical erosion under the effect of a stream of matter or radiation (Journal Officiel de la République Française [Official Journal of the French Republic] of Sep. 22, 2000). This is in particular the case with materials which are part of heat shields intended for the aerospace industry and the walls of nozzles of propulsion engines. Typically, in this case, the external layer of the ablative material which is directly in contact with the environment undergoes, under the effect of the heat, a chemical transformation, and also a recession linked to this transformation. This external layer therefore radiates toward the exterior and its chemical transformation consumes energy. These two effects contribute to a lower transmission of heat toward the internal layers of the material and therefore to a thermal insulation of the underlying structure. A good ablative material must be such that its chemical transformation under the effect of heat is endothermic, its thermal conductivity is low in the stationary and/or in the transitional state and its chemical transformation is not accompanied by too rapid a recession. In particular, in order to accomplish the latter point, the chemical transformation of the ablative material is accompanied by the formation of a carbon-based or silicon-based crust originating from the pyrolysis of the resin.

This is in particular obtained for resins which have a high coke content. The coke content is defined as the mass of residue that is obtained when a sample of an organic polymer is decomposed by pyrolysis, at a temperature of 900° C. under an inert (nitrogen or argon) atmosphere, relative to the initial mass of this sample. The most beneficial resins have a coke content of greater than 50%.

Phenolic resins in general have such a coke content and are obtained by polycondensation of monomers resulting from petrochemistry: phenol and formaldehyde, which is why they are also known as phenol-formaldehyde resins or formophenolic resins. The precursors of phenolic resins, phenol and formaldehyde, are respectively CMR 2 and 1B. These two compounds are therefore monitored under European Parliament Regulation (EC) No. 1907/2006 (REACH) which aims to better protect human health and the environment against the risks associated with chemical substances. Furthermore, it proves the case that the polycondensation of the phenol and formaldehyde is never complete, hence the presence of volatile compounds and of water molecules which are very difficult to eliminate if a well-defined thermal cycle is not carried out during this polycondensation and which can result in materials that are porous in their natural state and also in degassing events during the lifetime of materials produced from phenolic resins. In point of fact, these degassing events can have very harmful consequences in certain applications such as, for example, aerospace applications.

Given the place that phenolic resins currently have in the plastics industry and the drawbacks thereof, new thermosetting resins which have properties similar to those of phenolic resins have been obtained from different precursors. Thus, patent application WO 2017/129661 describes such resins and the processes for producing them. Such resins have a coke content of greater than 50% and can therefore be used as ablative materials. The precursors used are in particular aromatic molecules bearing propargyl ether functions. However, the excessive energy released during their polymerization could cause thermal runaway during the production of composite materials. Thus, in order to obtain an enthalpy of polymerization of approximately 800-900 J/g with the lowest possible loss of mass during the polymerization, it is necessary, in the process described in this application, to maintain a lengthy thermal treatment during the polymerization in order to prevent any thermal runaway. This solution is not therefore optimized with respect to the production of thick parts which can be up to several tens of millimeters thick.

The inventors have realized that it is possible to reduce the energy released during the polymerization of resins comprising propargyl ether end groups by a factor of 6 by conversion of the propargyl ether function to a chromene function, and thus to reduce the enthalpy of polymerization to a value <500 J/g.

Patent application EP0350747 describes a process for preparing thermosetting resins from chromene precursors, themselves obtained by conversion of aromatic propargyl ethers by means of a catalysis with copper salts or zinc salts. However, the solvents explicitly described in this application on page 5, lines 27-28, which are diethylbenzene, diisopropylbenzene, dichlorobenzene, trichlorobenzene and tetralin, have a negative impact on the environment and/or human health. In addition, some of the aromatic propargyl ethers indicated as preferred in this application, such as propargylated bisphenol A, do not make it possible to obtain thermosetting resins having a coke content of greater than 50%.

The inventors have discovered, surprisingly, that some aromatic propargyl ethers are particularly beneficial for the production of thermosetting resins having a coke content of greater than 50% and for obtaining an enthalpy of polymerization <500 J/g when they are first converted into chromenes by homogeneous catalysis with copper salts, even more so if they are derived from compounds that can be biosourced, such as resorcinol, eugenol, coupled eugenol and coupled isoeugenol. They have also discovered that it is possible for these particular aromatic propargyl ethers to use anisole as solvent during this catalysis, anisole being a better solvent for human health as recommended by the CHEM21 initiative (public-private consortium targeting the development of sustainable methods for the pharmaceutical industry). In particular, anisole can be used at a temperature of less than 185° C. for the conversion of propargylated resorcinol into chromene with homogeneous catalysis with copper salts, thereby avoiding the formation of an insoluble precipitate.

The present invention thus relates to a process for producing chromenes intended for the preparation of thermosetting resins, comprising the step of converting an aromatic propargyl ether of general formula (I) below:

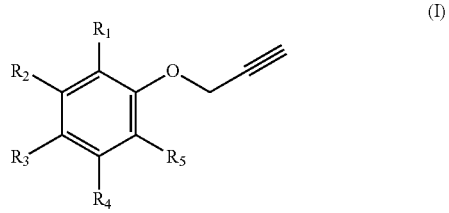

wherein:

$R_1$ and $R_5$ represent, independently of one another, a hydrogen atom, or a $C_2$-$C_6$ alkene, $C_2$-$C_6$ alkyne, O—($C_1$-$C_6$)alkyl, O—($C_2$-$C_6$)alkene or O—($C_2$-$C_6$)alkyne group, on condition that at least one of $R_1$ and $R_5$ represents a hydrogen atom;

$R_2$ and $R_4$ represent, independently of one another, a hydrogen atom, a $C_2$-$C_6$ alkene group, a $C_2$-$C_6$ alkyne group such as a propargyl, an O—($C_1$-$C_6$)alkyl group, an O—($C_2$-$C_6$)alkene group or an O—($C_2$-$C_6$)alkyne group, such as an O-propargyl;

and $R_3$ represents a hydrogen atom, an O—($C_1$-$C_6$)alkyl group or a $C_2$-$C_6$ alkene group, the alkene group being optionally substituted with a group of general formula (II) below:

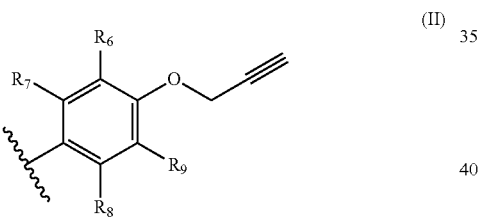

wherein:

$R_6$ and $R_9$ represent, independently of one another, a hydrogen atom, or a $C_2$-$C_6$ alkene, $C_2$-$C_6$ alkyne, O—($C_1$-$C_6$)alkyl, O—($C_2$-$C_6$)alkene or O—($C_2$-$C_6$)alkyne group, on condition that at least one of $R_6$ and $R_9$ represents a hydrogen atom;

and $R_7$ and $R_8$ represent, independently of one another, a hydrogen atom, a $C_2$-$C_6$ alkene group, a $C_2$-$C_6$ alkyne group such as a propargyl, an O—($C_1$-$C_6$)alkyl group, an O—($C_2$-$C_6$)alkene group or an O—($C_2$-$C_6$)alkyne group such as an O-propargyl;

on condition that at least one of $R_1$, $R_2$, $R_3$, $R_4$ and $R_5$ does not represent a hydrogen atom or an O—($C_1$-$C_6$)alkyl group;

and the cis/trans isomers thereof and the optical isomers thereof, and racemic mixtures thereof into a chromene by homogeneous catalysis with copper salts in anisole at a temperature of between 100 and 170° C., beneficially between 120 and 160° C., more beneficially between 140 and 160° C., even more beneficially between 152 and 157° C., in particular at 155° C.

For the purposes of the present invention, the term "$C_2$-$C_6$ alkene group" is intended to mean any linear or branched alkene group having from 2 to 6 carbon atoms, in particular the vinyl group, the allyl group or the but-2-enyl group.

For the purposes of the present invention, the term "$C_2$-$C_6$ alkyne group" is intended to mean any linear or branched alkyne group having from 2 to 6 carbon atoms, in particular the ethynyl group or the propargyl group.

For the purposes of the present invention, the term "O—($C_1$-$C_6$)alkyl group" is intended to mean any linear or branched O-alkyl group having from 1 to 6 carbon atoms, in particular the methoxy or ethoxy group.

For the purposes of the present invention, the term "O—($C_2$-$C_6$)alkene group" is intended to mean any linear or branched O-alkene group having from 2 to 6 carbon atoms.

For the purposes of the present invention, the term "O—($C_2$-$C_6$)alkyne group" is intended to mean any linear or branched O-alkyne group having from 2 to 6 carbon atoms, in particular the O-propargyl group.

Beneficially, the aromatic propargyl ether of general formula (I) is chosen from the group consisting of propargylated resorcinol, propargylated eugenol, propargylated coupled eugenol, propargylated coupled isoeugenol, propargylated isoeugenol and mixtures thereof and the cis/trans isomers thereof and the optical isomers thereof and racemic mixtures thereof, and more beneficially it is propargylated resorcinol.

These products are well known to those skilled in the art and can be prepared by well-known processes, such as those described in application WO 2017/129661. They have the benefit of it also being possible for them to be derived from compounds that can be biosourced, such as resorcinol, eugenol, coupled eugenol, isoeugenol and coupled isoeugenol.

Propargylated resorcinol thus has the general formula below:

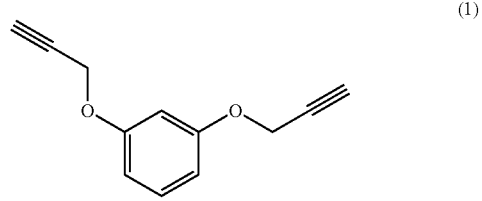

Propargylated eugenol thus has the general formula below:

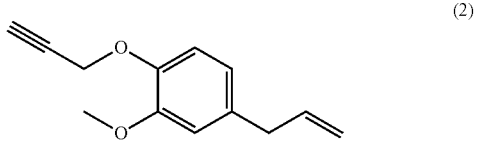

Propargylated coupled eugenol thus has the general formula below:

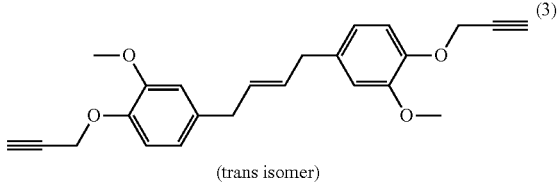

(trans isomer)

or the general formula below:

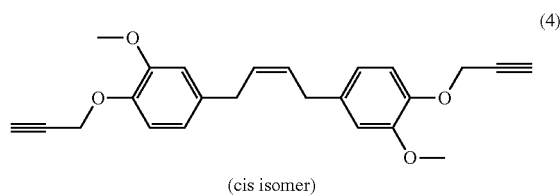

(cis isomer) (4)

or a mixture of these two isomers.

Propargylated isoeugenol thus has the general formula below:

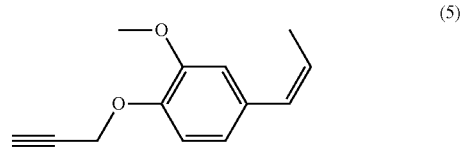

(5)

Propargylated coupled isoeugenol thus has the general formula below:

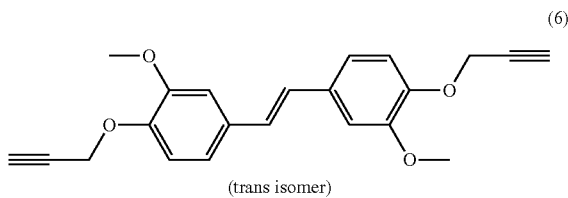

(trans isomer) (6)

or the general formula below

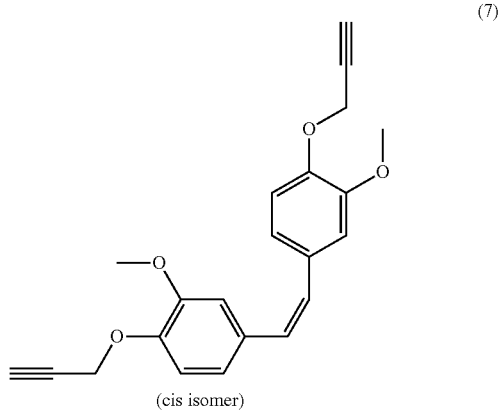

(cis isomer) (7)

or a mixture of these two isomers.

The solvent used in the process according to the invention is thus anisole. Beneficially, the process according to the present invention comprises an additional step of eliminating the anisole, in particular by evaporation, more particularly after the optional step of eliminating the catalyst.

The catalyst of the process according to the present invention is a copper salt.

Any copper (I) or copper (II) salt may be used, but the salt is beneficially chosen from copper halides, copper acetates, copper bromides, copper chlorides, copper cyanides, copper fluorides, copper nitrates, copper phosphates, copper sulfates, copper alkoxides, copper trifluoroacetates, copper methanesulfonates, copper benzenesulfonates, copper p-toluenesulfonates, copper tetrafluoroborates, copper hexafluoroborates, copper acetylacetonates and copper gluconates. Beneficially, the copper salt is a copper chloride, in particular chosen from CuCl and $CuCl_2$, it is beneficially CuCl.

Beneficially, the catalyst content in the reaction medium is between 10 and 10 000 ppm, more beneficially between 500 and 1500 ppm, even more beneficially between 300 and 1500 ppm, it is in particular 1000 ppm. The catalyst can be eliminated at the end of the process or left in the reaction medium. The process can thus comprise an additional step of eliminating the catalyst from the reaction medium, beneficially by processes well known to those skilled in the art.

The process according to the invention is beneficially carried out under an inert atmosphere (nitrogen or argon, for example).

The reaction time depends on the reaction conditions, such as the aromatic propargyl ethers used, the reaction temperature, the catalyst content. Beneficially, the process according to the invention lasts between 1 and 1000 hours, more beneficially between 2 and 50 hours, even more beneficially between 3 and 48 hours.

The inventors have noticed that it is not necessary to have a quantitative conversion of the propargyl ether functions into chromene in order to obtain an enthalpy of polymerization of less than 500 J/g. Indeed, the energy released during the polymerization for a given substrate is dependent on its molar mass and its functionality. By using the energy released per propargyl function and per chromene function, combined with the molar mass of each substrate, it is possible to theoretically determine the maximum residual propargyl function percentage in order to be below 500 J/g. These values were compared to the experimental values obtained and are similar. Thus, table 1 hereinafter indicates the theoretical residual propargyl function percentage in order to be below 500 J/g of enthalpy of reaction during the polymerization. The theoretical residual propargyl function percentage is calculated in the following way: (number of moles of propargyl functions at the end of the reaction)/(number of moles of propargyl functions before the beginning of the reaction)×100.

TABLE 1

| Substrate | M (g/mol) | Propargyl group functionality | Theoretical residual propargyl function molar percentage to reach an enthalpy of 500 J/g |
|---|---|---|---|
| Propargylated resorcinol | 186.21 | 2 | 11 |
| Propargylated coupled eugenol | 376.44 | 2 | 39 |
| Propargylated coupled isoeugenol | 348.39 | 2 | 35 |

Thus, beneficially, the conversion of the aromatic propargyl ethers into chromene by the process according to the present invention is not total and the chromene obtained comprises residual propargyl functions. Beneficially, the molar percentage of residual propargyl functions of the chromene is less than 11% when the aromatic propargyl ether of general formula (I) is propargylated resorcinol, the molar percentage of residual propargyl functions of the chromene is less than 39% when the aromatic propargyl ether of general formula (I) is propargylated coupled eugenol and the molar percentage of residual propargyl functions of the chromene is less than 35% when the aromatic propargyl ether of general formula (I) is propargylated coupled isoeugenol.

In the case where the aromatic propargyl ether of general formula (I) is propargylated resorcinol, the chromene obtained by means of the process according to the invention may have the formula C and/or D below; it is beneficially a mixture of formulae C and D.

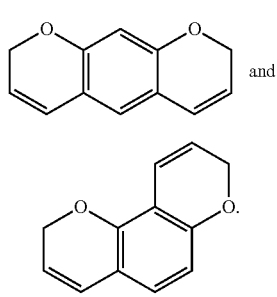

In particular, the molar proportion of chromene of formula D in the mixture after total conversion is between 50 and 55% and that of chromene of formula C is between 45 and 50%; in particular, it is 45% of chromene of formula C and 55% of chromene of formula D.

In the case where the aromatic propargyl ether of general formula (I) is propargylated resorcinol, the chromene obtained by means of the process according to the invention may also have the formula A and/or B below.

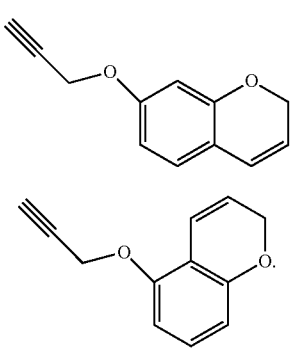

However, these molecules are in general rapidly converted into compounds of formula C and D.

Beneficially, the molar yield of the reaction for conversion of the aromatic propargyl ether into chromene is between 85 and 99%, in particular between 90 and 99%.

The present invention also relates to a process for preparing a material made of thermoset resin, comprising the following successive steps:
 a) carrying out the process according to the present invention, beneficially as described above;
 b) polymerizing the reaction product obtained in step a) so as to obtain the material made of thermoset resin;
 c) recovering the material made of thermoset resin obtained in step b).

In accordance with the invention, the polymerization of the resin can be carried out by any means capable of inducing polymerization/crosslinking of the chromene and, in particular, by application of a heat treatment or a light treatment (visible, UV or IR light).

In particular, step b) is carried out by heat treatment, beneficially at a temperature of between 80° C. and 180° C., more beneficially by means of several stationary heating phases (in particular 5), without the addition of other components, such as for example 2 h at 80° C., 2 h at 100° C., 2 h at 120° C., 2 h at 140° C. and 2 h at 180° C. or 1 h at 80° C., 1 h at 100° C., 1 h at 120° C., 1 h at 140° C., 1 h at 160° C., 1 h at 180° C., 1 h at 200° C.

More particularly, the process according to the invention can comprise, between steps b) and c), an annealing step b1) at a temperature above 200° C. but below the resin degradation temperature, for example at 220° C. This step makes it possible to improve the thermomechanical properties of the resin.

Beneficially, the enthalpy of polymerization of step b) is less than 500 J/g.

Beneficially, the coke content of the thermoset resin obtained in step b) is greater than 50%.

In one beneficial embodiment, the material made of thermoset resin is a material forming the matrix of a composite material of the type comprising a matrix in which there is a reinforcement.

The reinforcement present in the composite material may be of various types. Thus, it may in particular be a reinforcement consisting of fibers, such as glass fibers, quartz fibers, carbon fibers, graphite fibers, silica fibers, metal fibers such as steel fibers or aluminum fibers, boron fibers, ceramic fibers such as silicon carbide or boron carbide fibers, synthetic organic fibers such as aramid fibers, polyethylene fibers, polyester fibers or poly(p-phenylene benzobisoxazole) fibers, more well-known under the acronym PBO, natural organic fibers such as hemp fibers, flax fibers or silk fibers, or else mixtures of such fibers; in which case, this reinforcement may be, depending on the nature of the fibers of which it is constituted, in the form of cut threads, ground fibers, continuous-filament mats, cut-filament mats, rovings, fabrics, knits, felts, etc., or else in the form of complexes produced by combining various types of flat materials.

It may also be reinforcement consisting of particles such as cork particles or refractory fillers of the tungsten, magnesium oxide, calcium oxide, alumina, silica, zirconium dioxide, titanium dioxide, beryllium oxide, etc., type.

Moreover, the production of the composite material, and therefore the addition of reinforcement in the resin, can be carried out by any of the composite-material techniques known to those skilled in the art, such as, for example, by impregnation, by simultaneous injection molding, by autoclave lay-up molding, by vacuum molding, by molding by low pressure injection of resin (or RTM for Resin Transfer Molding), by low-pressure "wet route" cold press molding, by compound injection molding (BMC for Bulk Molding Compound), by molding by compression of preimpregnated mats (or SMC for Sheet Molding Compound), by filament winding, by centrifugal molding or by pultrusion, impregnation being preferred in the case where the reinforcement consists of fibers.

Beneficially, the composite material is an ablative composite material and, more specifically, a thermal protection ablative composite material, in particular for the aerospace industry.

The present invention will be understood more clearly on reading the description of the examples which follow and which are given by way of nonlimiting indication.

EXAMPLE 1

Conversion of Proparaylated Resorcinol and Preparation of the Resin according to the Invention Synthesis of Proparaylated Resorcinol 10 g (0.091 mol) of resorcinol (Alfa Aesar) are dissolved in 50 ml of dimethylsulfoxide (DMSO), 50 g (0.363 mol) of potassium carbonate ($K_2CO_3$) are ground and then added with magnetic stirring and the medium heated to 70° C. (ext). 14.45 ml (2.2 eq.) of propargyl chloride (ABCR) are added dropwise. The reaction is monitored by TLC with a 7:3 petroleum ether:diethyl ether (volume) eluent. After filtration and dilution in 100 ml of ethyl acetate, the medium is extracted with 3×100 ml of brine. The organic phase is dried over $MgSO_4$, filtered and concentrated under reduced pressure. The compound is purified by vacuum distillation (T° C.=120° C., 4.5 Pa). The yield is 77.4%.

Conversion of Proparaylated Resorcinol 10 grams (0.054 mol) of propargylated resorcinol previously obtained, 1000 ppm of CuCl and 100 ml of anisole are introduced into a Schlenk tube surmounted by a condenser. Bubbling of argon is carried out for 10 minutes and the medium is stored under argon. The Schlenk tube is placed in an oil bath preheated to 155° C. and the reaction is continued at reflux for 4 hours. After 4 hours, the medium is filtered through a 0.20 µm PTFE filter in order to remove the precipitates possibly formed. The anisole is evaporated off under reduced pressure by means of a bulb oven and a vane pump. The proportion of residual propargyl ether function is estimated to be 5% by $^1H$ NMR. The yield is 99%. The proportion of residual propargyl ether functions of less than 11% is in accordance with the set specifications.

Polymerization of the Chromene Derived from the Propargylated Resorcinol

The polymerization of the propargyl-chromene mixtures is carried out by gradual increase in the temperature. In the case of a propargyl resorcinol-chromene mixture with a proportion of residual propargyl ether functions of less than 11% as obtained previously, the heat treatment applied is the following: 2 h at 80° C., 2 h at 100° C., 2 h at 110° C., 2 h at 120° C., 2 h at 130° C. and 2 h at 150° C.

Annealing at 220° C. can be carried out in order to increase the thermomechanical properties.

The coke content obtained before and after annealing is 65.9% and the enthalpy of reaction is 420 J/g.

EXAMPLE 2

Conversion of Propargylated Resorcinol and Preparation of the Resin according to the Invention Conversion of Propargylated Resorcinol 50 grams (0.269 mol) of propargylated resorcinol obtained according to the process indicated in example 1, 1000 ppm of CuCl and 150 ml of anisole are introduced into a 500 ml two-necked flask equipped with a magnetic stirrer and surmounted by a condenser. Bubbling of argon is carried out for 10 minutes and the medium is stored under argon. The medium is placed in an oil bath preheated to 155° C. and the reaction is continued at reflux for 7 hours until the total conversion of the propargyl ether functions into chromene functions. After 7 hours, the medium is filtered through a cellulose filter in order to remove the precipitates possibly formed. The anisole is evaporated off by distillation under reduced pressure. The proportion of residual propargyl ether functions is estimated to be less than 1% by $^1H$ NMR. The yield is 97%. The proportion of residual propargyl functions of less than 11% is in accordance with the set specifications.

Polymerization of the Chromene derived from the Proparaylated Resorcinol

The process carried out is identical to that described in example 1. The coke content obtained before and after annealing is 65.3% and the enthalpy of reaction is 300 J/g.

EXAMPLE 3

Conversion of Propargylated Eugenol and Preparation of the Resin according to the Invention Synthesis of Proparaylated Eugenol Eugenol (Sigma Aldrich) (200 g), $K_2CO_3$ (211 g) and dimethylformamide (DMF) (2000 ml) are introduced into a 6 L round-bottomed flask and are heated to 75° C. with mechanical stirring. Propargyl chloride (ABCR) at 70% in toluene (158.5 ml) is added dropwise by means of a dropping funnel and the reaction medium is heated and stirred at 75° C. overnight. The reaction is monitored by TLC with a 7:3 petroleum ether/diethyl ether (volume) eluent. After reaction, the reaction medium is filtered and then diluted and rinsed with ethyl acetate. The organic phase is rinsed with water until decoloring of the aqueous phase is obtained (4 times). The organic phase is dried over $MgSO_4$ and concentrated under vacuum. The yield of the crude product is 93%. The compound is purified by vacuum distillation (p=4.5 Pa and T° C.=60° C.). The yield of the distilled compound is 90%.

Conversion of Propargylated Eugenol 1 g (0.005 mol) of propargylated eugenol obtained previously, 1000 ppm of CuCl and 3 ml of anisole are introduced into a Schlenk tube. Bubbling with argon is carried out for 10 minutes, and the reaction medium is stored under argon with a coolant. The medium is introduced into an oil bath preheated to 155° C. The reaction is left at reflux and monitored by regular sampling and $^1H$ NMR analysis. After 23 h, the anisole is evaporated off in a rotary evaporator. The proportion of residual propargyl ether functions is estimated to be less than 1% by $^1H$ NMR. The yield is 90%.

Polymerization of the Chromene Derived from the Propargylated Eugenol

The process carried out is identical to that described in example 1 for propargylated resorcinol.

EXAMPLE 4

Conversion of Propargylated Coupled Eugenol and Preparation of the Resin according to the Invention Synthesis of the Coupled Eugenol 26.675 g (0.1625 mol) of eugenol (Sigma Aldrich) are introduced into a 50 ml three-necked round-bottomed flask with a magnetic stirrer. 0.1337 g (0.1 mol %) of $1^{st}$-generation Grubbs catalyst (Sigma Aldrich) is introduced using a pill bottle with argon countercurrent. The medium is directly placed under a strong vacuum (3 kPa) and left to stir for 12 h. A $^1H$ NMR spectrum of the crude product is performed in order to determine the eugenol conversion. The conversion is 67 mol % of coupled eugenol compounds, the remaining 37 mol % being a mixture of unreacted eugenol and its isomer, isoeugenol. The stochiometric proportion is evaluated, by $^1H$ NMR, at 34.3%/65.7% for the cis- and trans-coupled eugenol compounds respectively. The medium is dissolved in a minimum amount of ether at reflux, then left to stand at ambient temperature. The solid is filtered under reduced pressure on a frit with a porosity of 4, then washed with 4×20 ml of cyclohexane. The solid is dried under a strong vacuum using a vane pump for 10 h. In order to remove the 1$^{st}$-generation Grubbs catalyst, the solid is dissolved in dichloromethane (DCM) and then filtered through celite. A black deposit is observed on the celite. The organic phase is dried under reduced pressure. The yield obtained is 25%.

Synthesis of the Propargylated Coupled Eugenol 3 g (0.010 mol) of coupled eugenol obtained previously is dissolved in 30 ml (10 eqm) of DMF. 5.52 g (4 eq.) of finely ground potassium carbonate ($K_2CO_3$) are added with magnetic stirring. 2.78 ml (2.5 eq.) of propargylated bromide (Alfa Aesar) (80 m % in toluene) are added by means of a dropping funnel. The magnetic stirring is maintained for 12 h. The completion of the reaction is monitored by TLC with a 50:50 petroleum ether:ethyl acetate (volume) eluent. After filtration of the $K_2CO_3$ and washing with DMF, an excess of distilled water (200 ml) is added in order to cause the product to precipitate. The solid is recovered. 200 ml of ethyl acetate are added to the medium for the extraction. The aqueous phase is discarded. The solid previously recovered is redissolved in the organic phase. The organic phase is washed three times with distilled water (3×100 ml) and once with brine (1×100 ml). The organic phase is dried over $MgSO_4$, filtered and concentrated under reduced pressure. The yield is 90%.

Conversion of the Propargylated Coupled Eugenol 0.5 g (0.001 mol) of propargylated coupled eugenol previously obtained, 1000 ppm of CuCl and 10 ml of anisole are introduced into a Schlenk tube. Bubbling with argon is carried out for 10 minutes, and the medium is stored under argon with a coolant. The Schlenk tube is introduced into an oil bath preheated to 155° C. The reaction is monitored by regular sampling and $^1$H NMR analysis. After 24 h of reaction, the anisole is evaporated off in a bulb oven by means of a vane pump. The proportion of residual propargyl ether functions is estimated to be 9% by $^1$H NMR. The yield is 97%. The proportion of residual propargyl ether functions of less than 39% is in accordance with the set specifications.

Polymerization of the Chromene Derived from the Propargylated Coupled Eugenol

The process carried out is identical to that described in example 1 for the propargylated resorcinol, with the exception of the fact that the heat treatment applied is the following: 1 h at 80° C., 1 h at 100° C., 1 h at 120° C., 1 h at 140° C., 1 h at 160° C., 1 h at 180° C., 1 h at 200° C.

EXAMPLE 5

Conversion of Propargylated Coupled Isoeugenol and Preparation of the Resin according to the Invention Synthesis of the Coupled Isoeugenol 0.0181 g (0.017%) of Grubbs II catalyst (UMICORE M2a) is introduced into a 50 ml round-bottomed flask with a magnetic stirrer, then 20 g (0.122 mol) of isoeugenol (Sigma Aldrich) are added. The medium is placed under an argon stream and heated to 90° C. The medium becomes solid after 3 minutes of reaction. After cooling, a $^1$H NMR spectrum of the crude product is performed in order to determine the conversion of the isoeugenol into stilbene. The degree of conversion is 90%. Only the trans-compound is observed. The product is recovered by suspension in 4 vol. of DCM, and the medium is refluxed for 1 hour until complete solubilization and then left to stand at ambient temperature overnight. The suspension is filtered on a frit and washed with 1 vol. of cyclohexane. The isolated yield is 67%.

Synthesis of the Propargylated Coupled Isoeugenol 10 g (0.037 mol) of eugenol stilbene previously obtained are dissolved in 100 ml (10 eqm) of DMF. 25 g (4.5 eq.) of finely ground potassium carbonate ($K_2CO_3$) are added with magnetic stirring. 10.23 ml (2.5 eq.) of propargyl bromide (Alfa Aesar) (80 m % in toluene) are added using a syringe. The magnetic stirring is maintained for 12 h. The completion of the reaction is monitored by TLC with a 50:50 petroleum ether:ethyl acetate (volume) eluent. The conversion is total after reaction overnight. The $K_2CO_3$ is filtered off and then washed with ethyl acetate. The compound is extracted with 2×100 ml of ethyl acetate. The organic phases are washed with 4×100 ml of brine. The organic phases are dried over $MgSO_4$, filtered and concentrated under reduced pressure. The yield of the product is 30%.

Conversion of the Propargylated Coupled Isoeugenol 1 g (0.003 mol) of propargylated coupled isoeugenol obtained previously, 1000 ppm of CuCl and 20 ml of anisole are introduced into a Schlenk tube. Bubbling with argon is carried out for 10 minutes, and the medium is stored under argon with a coolant. The Schlenk tube is introduced into an oil bath preheated to 155° C. The reaction is monitored by regular sampling and $^1$H NMR analysis. After 48 h of reaction, the anisole is evaporated off in a bulb oven by means of a vane pump. The viscosity of the resin did not make it possible to completely evaporate off the reaction solvent. The proportion of residual propargyl ether functions is estimated to be 12% by $^1$H NMR. The proportion of residual propargyl ether functions of less than 39% is in accordance with the set specifications.

Polymerization of the Chromene Derived from the Propargylated Coupled Isoeugenol The process carried out is identical to that described in example 1.

EXAMPLE 5

Conversion of Propargylated Isoeugenol and Preparation of Resin according to the Invention Synthesis of the Propargylated Isoeugenol 20 g (0.130 mol) of isoeugenol (Sigma Aldrich) are solubilized in 100 ml (5 eqm) of DMF. 33.67 g (2 eq.) of finely ground potassium carbonate ($K_2CO_3$) are added with magnetic stirring. 20.35 ml (1.5 eq.) of propargyl bromide (Alfa Aesar) (80 m % in toluene) are added by means of a dropping funnel. The magnetic stirring is maintained for 12 h. The completion of the reaction is monitored by TLC with a 70:30 petroleum ether:ethyl acetate (volume) eluent. After filtration of the $K_2CO_3$ and washing with ethyl acetate, 100 ml of ethyl acetate are added to the medium for the extraction. The organic phase is washed 3 times with distilled water (3×100 ml) and once with brine (1×100 ml). The organic phase is dried over $MgSO_4$, filtered and concentrated under reduced pressure. The yield is 91%.

The compound is purified by vacuum distillation using a bulb oven (p=15 Pa and T° C. heating=140° C.). The compound is recovered in the form of white crystals. The overall yield after purification is 73%.

Conversion of the Proparaylated Isoeugenol 1 g (0.005 mol) of propargylated isoeugenol obtained previously, 1000 ppm of CuCl and 5 ml of anisole are introduced into a Schlenk tube surmounted by a condenser. Bubbling with argon is carried out for 10 minutes and the medium is stored under argon. The Schlenk tube is introduced into an oil bath preheated to 155° C. and the reaction is left at reflux. The progression of the reaction is monitored by regular sampling and $^1$H NMR analysis. After 30 hours of reaction, the anisole is evaporated off by distillation at 80° C. by means of a bulb oven. The yield is 98%. The proportion of residual propargyl ether functions is estimated to be 10% by $^1$H NMR.

Polymerization of the Chromene Derived from the Proparaylated Isoeugenol

The process carried out is identical to that described in example 1.

The invention claimed is:

1. A process for producing chromenes intended for the preparation of thermosetting resins, comprising the step of converting an aromatic propargyl ether of general formula (I) below:

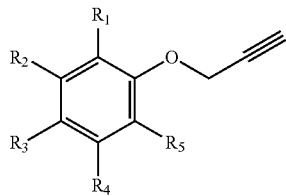

(I)

wherein:

$R_1$ and $R_5$ represent, independently of one another, a hydrogen atom, or a $C_2$-$C_6$ alkene, $C_2$-$C_6$ alkyne, O—($C_1$-$C_6$)alkyl, O—($C_2$-$C_6$)alkene or O—($C_2$-$C_6$) alkyne group, on condition that at least one of $R_1$ and $R_5$ represents a hydrogen atom;

$R_2$ and $R_4$ represent, independently of one another, a hydrogen atom, a $C_2$-$C_6$ alkene group, a $C_2$-$C_6$ alkyne group, an O—($C_1$-$C_6$)alkyl group, an O—($C_2$-$C_6$)alkene group or an O—($C_2$-$C_6$)alkyne group;

and $R_3$ represents a hydrogen atom, an O-($C_1$-$C_6$)alkyl group or a $C_2$-$C_6$ alkene group, the alkene group being optionally substituted with a group of general formula (II) below:

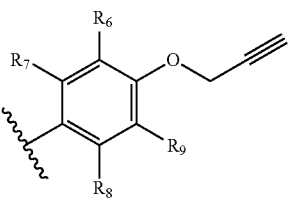

(II)

wherein:

$R_6$ and $R_9$ represent, independently of one another, a hydrogen atom, or a $C_2$-$C_6$ alkene, $C_2$-$C_6$ alkyne, O—($C_1$-$C_6$)alkyl, O—($C_2$-$C_6$)alkene or O—($C_2$-$C_6$) alkyne group, on condition that at least one of $R_6$ and $R_9$ represents a hydrogen atom;

and $R_7$ and $R_8$ represent, independently of one another, a hydrogen atom, a $C_2$-$C_6$ alkene group, a $C_2$-$C_6$ alkyne group, an O—($C_1$-$C_6$)alkyl group, an O—($C_2$-$C_6$)alkene group or an O—($C_2$-$C_6$)alkyne group;

on condition that at least one of $R_1$, $R_2$, $R_3$, $R_4$ and $R_5$ does not represent a hydrogen atom or an O—($C_1$-$C_6$)alkyl group;

and the cis/trans isomers thereof and the optical isomers thereof, and racemic mixtures thereof into a chromene by homogeneous catalysis with copper salts in anisole at a temperature of between 100 and 170° C.

2. The process as claimed in claim 1, wherein the aromatic propargyl ether of general formula (I) is chosen from the group consisting of propargylated resorcinol, propargylated eugenol, propargylated coupled eugenol, propargylated coupled isoeugenol, propargylated isoeugenol and mixtures thereof and the cis/trans isomers thereof and the optical isomers thereof and racemic mixtures thereof.

3. The process as claimed in claim 2, wherein the molar percentage of residual propargyl functions of the chromene is less than 11% when the aromatic propargyl ether of general formula (I) is propargylated resorcinol, the molar percentage of residual propargyl functions of the chromene is less than 39% when the aromatic propargyl ether of general formula (I) is propargylated coupled eugenol and the molar percentage of residual propargyl functions of the chromene is less than 35% when the aromatic propargyl ether of general formula (I) is propargylated coupled isoeugenol.

4. The process as claimed in claim 2, wherein the aromatic propargyl ether of general formula (I) is propargylated resorcinol and wherein the chromene obtained has the formula C and/or D below

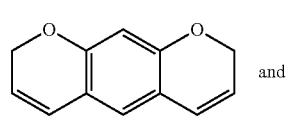

(C)

and

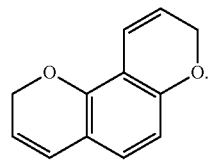

(D)

5. The process as claimed in claim 4, wherein the chromene obtained is a mixture of the formulae C and D.

6. The process as claimed in claim 2, wherein the aromatic propargyl ether of general formula (I) is propargylated resorcinol.

7. The process as claimed in claim 1, which lasts between 1 and 1000 hours.

8. The process as claimed in claim 7, which lasts between 2 and 50 hours.

9. The process as claimed in claim 1, wherein the catalyst is chosen from CuCl and $CuCl_2$.

10. The process as claimed in claim 9, wherein the catalyst is CuCl.

11. The process as claimed in claim 1, wherein the catalyst content in the reaction medium is between 10 and 10 000 ppm.

12. The process as claimed in claim 11, wherein the catalyst content in the reaction medium is between 500 and 1500 ppm.

13. A process for preparing a material made of thermoset resin, comprising the following successive steps:
   a) carrying out the process as claimed in claim 1;
   b) polymerizing the reaction product obtained in step a) so as to obtain the material made of thermoset resin;
   c) recovering the material made of thermoset resin obtained in step b).

14. The process as claimed in claim 13, wherein the enthalpy of polymerization of step b) is less than 500 J/g.

15. The process as claimed in claim 13, wherein the coke content of the thermoset resin obtained in step c) is greater than 50%.

16. The process as claimed in claim 1, wherein the temperature is of between 120 and 160° C.

* * * * *